(12) United States Patent
Lee et al.

(10) Patent No.: US 10,632,050 B2
(45) Date of Patent: Apr. 28, 2020

(54) VESICLE FOR ENHANCING SKIN ABSORPTION, AND METHOD OF PREPARING THE SAME

(71) Applicant: COSMAX INC., Hwaseong-si, Gyeonggi-do (KR)

(72) Inventors: Jun Bae Lee, Yongin-si (KR); Ji Hui Jang, Hanam-si (KR); Min Joo Noh, Seongnam-si (KR); Eun Seon Jang, Seongnam-si (KR); Su Ji Kim, Seongnam-si (KR); Myeong Sam Park, Seoul (KR)

(73) Assignee: COSMAX INC., Hwaseong-si, Gyeonggi-do (KR)

(*) Notice: Subject to any disclaimer, the term of this patent is extended or adjusted under 35 U.S.C. 154(b) by 0 days.

(21) Appl. No.: 16/351,678

(22) Filed: Mar. 13, 2019

(65) Prior Publication Data

US 2019/0336414 A1     Nov. 7, 2019

(30) Foreign Application Priority Data

May 4, 2018 (KR) .................. 10-2018-0052134

(51) Int. Cl.
| | | |
|---|---|---|
| *A61K 8/14* | (2006.01) | |
| *A61K 8/34* | (2006.01) | |
| *A61K 8/42* | (2006.01) | |
| *A61K 8/55* | (2006.01) | |
| *A61K 8/68* | (2006.01) | |
| *A61K 8/86* | (2006.01) | |
| *A61Q 19/00* | (2006.01) | |

(52) U.S. Cl.
CPC ............ *A61K 8/14* (2013.01); *A61K 8/345* (2013.01); *A61K 8/42* (2013.01); *A61K 8/553* (2013.01); *A61K 8/86* (2013.01); *A61Q 19/00* (2013.01); *A61K 2800/592* (2013.01)

(58) Field of Classification Search
None
See application file for complete search history.

(56) References Cited

U.S. PATENT DOCUMENTS

| | | | | |
|---|---|---|---|---|
| 2005/0287095 A1* | 12/2005 | Fujiwara | .................. | A61K 8/14 424/70.13 |
| 2010/0330132 A1* | 12/2010 | Inokuchi | .................. | A61K 8/02 424/401 |
| 2014/0363475 A1* | 12/2014 | Tanishima | ............... | A61K 8/31 424/401 |
| 2016/0199269 A1* | 7/2016 | Lee | ......................... | A61Q 19/00 514/78 |
| 2016/0213579 A1* | 7/2016 | Lee | ......................... | A61Q 19/00 |

FOREIGN PATENT DOCUMENTS

| | | |
|---|---|---|
| KR | 1020080106618 A | 12/2008 |
| KR | 1020110076068 A | 7/2011 |
| KR | 1020130122935 A | 11/2013 |
| KR | 1020130134532 A | 12/2013 |
| KR | 1020180032479 A | 3/2018 |
| WO | 2012056956 A1 | 5/2012 |

OTHER PUBLICATIONS

Machine-assisted English translation for KR 10-2013-0122935 (Tanaka). (Year: 2013).*
Sep. 5, 2018—056610812 Korean OA dated Aug. 21, 2018.
Sep. 5, 2018—087423986 Korean NOA dated Dec. 19, 2018.

\* cited by examiner

*Primary Examiner* — Sin J Lee
(74) *Attorney, Agent, or Firm* — Buchanan Ingersoll & Rooney PC (57) ABSTRACT

A method of preparing a vesicle for skin absorption enhancement, a vesicle prepared using the method, and a cosmetic composition including the vesicle are provided. The vesicle preparation method may provide a skin absorption enhancement effect and may be used to prepare vesicles with improved formulation stability. The vesicle prepared using the method may be safe without skin irritation and have an improved skin absorption effect due to the use of a ceramide as a skin absorption enhancer, and may have improved formulation stability due to use of a nonionic surfactant and a phospholipid. Accordingly, the vesicle may be used in cosmetic compositions for enhancing skin absorption of bioactive ingredients such as functional ingredients.

8 Claims, 4 Drawing Sheets

VESICLE FOR ENHANCING SKIN ABSORPTION, AND METHOD OF PREPARING THE SAME

CROSS-REFERENCE TO RELATED APPLICATION

This application claims the benefit of Korean Patent Application No. 10-2018-0052134, filed on May 4, 2018, in the Korean Intellectual Property Office, the disclosure of which is incorporated herein in its entirety by reference.

BACKGROUND

1. Field

One or more embodiments relate to a method of preparing a vesicle for enhancing skin absorption, a vesicle prepared using the method, and a cosmetic composition including the vesicle.

2. Description of the Related Art

Skin absorption of active ingredients may be divided into the following three ways depending on the penetration mode through the stratum corneum (or horny layer) of the skin: an intercellular pathway through intercellular lipid layer of the stratum corneum; an intracellular pathway directly through corneocytes; and a follicular pathway. Of these three ways, the intercellular pathway is known as the major skin absorption pathway. Accordingly, the components and structures of the intercellular lipids in the stratum corneum are very important for the skin absorption of active ingredients.

The intercellular lipids of the stratum corneum are known to consist of approximately 50% of ceramides, 20% to 25% of cholesterol, 20% to 25% of free fatty acids, 10% of cholesterol esters, 1% to 2% of cholesterol sulfate, and a small amount of phospholipids. These intercellular lipid components are known to have layered structures called lamellar structures (Non-patent document 1), in which there is orthorhombic and hexagonal packing. In particular, the orthorhombic structure, which is tightly packed, is considered the most significant factor inhibiting the transfer of substances through the intercellular lipid layer of the stratum corneum. In this regard, the intercellular lipids of the stratum corneum, especially ceramides which are considered the major constituent of the intercellular lipids, play an important role in skin barrier function, but also have a contradictory function of suppressing skin absorption of active ingredients.

To overcome the suppressed skin absorption through the intercellular lipids of the stratum corneum, various chemical enhancers have been introduced. Chemical enhancers may facilitate skin absorption mainly by damaging the layered structure and packing structure of the intercellular lipids or dissolving the stratum corneum intercellular lipids themselves. Among raw materials available in the cosmetics field, common chemical enhancers include menthol, ethanol, and various surfactants (Non-patent document 2). However, these components may damage the stratum corneum intercellular lipid structure itself and are not considered desirable chemical enhancers.

SUMMARY

As a result of research aimed at overcoming the drawbacks of the related art, the inventors found out that vesicles containing an intercellular lipid component may facilitate skin absorption of active ingredients without damage to the intercellular lipids of the stratum corneum of skin, thereby completing the present disclosure.

Additional aspects will be set forth in part in the description which follows and, in part, will be apparent from the description, or may be learned by practice of the presented embodiments.

According to an aspect of the disclosure, a method of preparing a vesicle includes: heating and dissolving a ceramide or a derivative thereof, a nonionic surfactant, a phospholipid, and a polyol to thereby prepare a lipid phase; preparing an water phase including a polyol and water; and mixing and stirring the lipid phase and the water phase to thereby prepare the vesicle.

According to another aspect of the disclosure, there is provided a vesicle for skin absorption enhancement prepared by using the above-described method.

According to another aspect of the disclosure, there is provided a cosmetic composition including the above-described vesicle.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the disclosure, a method of preparing a vesicle includes: heating and dissolving a ceramide or a derivative thereof, a nonionic surfactant, a phospholipid, and a polyol to thereby prepare a lipid phase; preparing an water phase including a polyol and water; and mixing and then stirring the lipid phase and the water phase to thereby prepare the vesicle.

As used herein, the term "vesicle" may refer to an artificially made vesicle structure, which may be used interchangeably with the term "liposome." The term "liposome" may refer to a spherical or elliptical structure made of lipids. When a molecule having both a hydrophobic fraction and a hydrophilic fraction is added to water, the hydrophilic fraction tends to move towards the water, while the hydrophobic fraction tends to avoid the water and thereby to coalesce on its own, thus resulting in a bilayer structure made of lipids. The vesicle may have a multilayered structure. The multilayered structure may include two or more lipid bilayers in one vesicle.

The term "ceramide" may refer to a compound consisting of sphingosine and a fatty acid, and is also called "N-acyl-sphingosine." Ceramides are a major component of the epidermis and the stratum corneum of skin. The ceramide may be any type commonly used in cosmetics, for example, a natural ceramide, a synthetic ceramide, or a derivative thereof. The ceramide may include at least one selected from the group consisting of ceramide EOP, ceramide NG, ceramide NS, ceramide NP, ceramide AS, and ceramide AP. The ceramide derivative may include any known derivative having properties similar to those of a ceramide.

Since known commonly used skin absorption enhancers, alcohols, menthols, urea, and the like may dissolve or modify intercellular lipid components to thereby facilitate skin absorption of active ingredients, damage to skin barriers and various stimuli or irritations may occur as a result of the changes to the intercellular lipid components. However, when a ceramide, which is similar to an intercellular lipid component, is used as a skin absorption enhancer, due to its affinity with the intercellular lipid components of the stratum corneum of skin, it may weaken the strong orthorhombic structure through intermolecular attraction with the intercellular lipid components such that fluidity of the lipid structure is enhanced, and thus provide a skin absorption enhancement effect for active ingredients without damage to the skin barrier, thereby overcoming the safety problems of the related art. In one or more embodiments, when menthol or ethanol is used as a skin absorption enhancer, the skin irritation index may be a light irritation level. However, when a ceramide is used as a skin absorption enhancer, the skin irritation index may be a low irritation level. Accordingly, among the skin absorption enhancer components, the ceramide was found to be the most suitable one in view of skin safety (Test Example 1).

The term "nonionic surfactant" may refer to a surfactant which does not dissociate into ions in water. The nonionic surfactant is not limited to specific types, and may be any type having intermolecular attraction with the phospholipid at an interface of the vesicle. The nonionic surfactant may be any nonionic surfactant commonly used in cosmetics. Non-limiting examples of the nonionic surfactant may include a polyoxyethylene alkyl ether ($RO(CH_2CH_2O)_mH$), a fatty acid sorbitan ester, a fatty acid diethanolamine ($RCON(CH_2CH_2OH)_2$), and an alkyl monoglyceryl ether ($ROCH_2CH(OH)CH_2OH$). These nonionic surfactants may be used alone or in a combination of two or more thereof. In one embodiment, the nonionic surfactant may be polyoxyethylene cholesteryl ether (PCE).

The term "phospholipid" may refer to an ester compound of phosphoric acid with a fatty acid. The phospholipid may include a glycerophospholipid including glycerol as a component, and a sphingophospholipid including a sphingosine base as a component. In one or more embodiments, the phospholipid may be lecithin or a hydrogenated lecithin.

The nonionic surfactant and the phospholipid may stabilize the formulation of vesicles. In particular, the formulation of the vesicle may be stabilized through intermolecular attraction between the ceramide, the nonionic surfactant, and the phospholipid at the interface of the vesicle.

The term "polyol," which may be used interchangeably with the term "polyhydric alcohol," may refer to an aliphatic compound having two or more hydroxyl groups (—OH). The polyol may be a glycerol, a glycol, or a combination thereof. However, embodiments are not limited thereto. The glycerol may be glycerin, diglycerin, polyglycerin, or a combination of two or more of the forgoing. However, embodiments are not limited thereto. The glycerin may be used interchangeably with the terms such as lysrine, propane-1,2,3-triol, 1,2,3-propenetriol, triphdroxypropane, and the like. The glycol may be propylene glycol, dipropylene glycol, butylene glycol, diethylene glycol, triethylene glycol, hexylene glycol, pentylene glycol, poly ethylene glycol, or a combination of two or more of the forgoing. However, embodiments are not limited thereto. In one or more embodiments, the polyol of the lipid phase and the polyol of the water phase may each independently be at least one selected from the group consisting of propylene glycol, dipropylene glycol, 1,3-butylene glycol, pentylene glycol, and 1,2-hexanediol.

An amount of the lipid phase may be chosen to be appropriate for formation of the vesicle. In one or more embodiments, the amount of the lipid phase may be about 5 wt % to about 35 wt %, about 5 wt % to about 25 wt %, about 5 wt % to about 20 wt %, about 5 wt % to about 15 wt %, about 10 wt % to about 25 wt %, about 10 wt % to about 20 wt %, or about 10 wt % to about 15 wt %, each based on a total weight of the vesicle composition including the lipid phase and the water phase.

An amount of the water phase may be chosen to be appropriate for formation of the vesicle in consideration of the amount of the lipid phase. In one or more embodiments, the amount of the water phase may be about 65 wt % to about 95 wt %, about 75 wt % to about 95 wt %, about 80 wt % to about 95 wt %, about 85 wt % to about 95 wt %, about 75 wt % to about 90 wt %, about 80 wt % to about 90 wt %, or about 85 wt % to about 90 wt %, each based on a total weight of the vesicle composition including the lipid phase and the water phase.

An amount of the ceramide or a derivative thereof may be, for example, about 0.1 wt % to about 5 wt %, about 0.1 wt % to about 3 wt %, about 0.1 wt % to about 1.5 wt %, about 0.1 wt % to about 1 wt %, or about 0.1 wt % to about 0.5 wt %, each based on a total weight of the vesicle composition including the lipid phase and the water phase. However, embodiments are not limited thereto. When the amount of the ceramide is less than 0.1 wt %, a skin absorption enhancement effect may be insufficient. When the amount of the ceramide exceeds 5 wt %, the vesicle may gelate or form a precipitate due to lack of solubility in water.

An amount of the nonionic surfactant may be, for example, about 0.1 wt % to about 5 wt %, about 0.1 wt % to about 3 wt %, about 0.1 wt % to about 1.5 wt %, or about 0.1 wt % to about 1 wt %, each based on a total weight of the vesicle composition including the lipid phase and the water phase. However, embodiments are not limited thereto.

An amount of the phospholipid may be, for example, about 0.1 wt % to about 5 wt %, about 0.1 wt % to about 3 wt %, about 0.1 wt % to about 1.5 wt %, or about 0.1 wt % to about 1 wt %, each based on a total weight of the vesicle composition including the lipid phase and the water phase. However, embodiments are not limited thereto.

A weight ratio of the nonionic surfactant to the phospholipid may be, for example, about 1:10 to about 10:1, and in some embodiments, about 2:8 to about 8:2, and in some other embodiments, about 3:7 to about 7:3, and in still other embodiments, about 2:8 to about 4:6. When the amounts of the nonionic surfactant and the phospholipid and the weight ratio of the nonionic surfactant to the phospholipid are not within the above-described ranges, the formulation stability of the vesicles may become poor.

An amount of the polyol of the lipid phase may be, for example, about 5 wt % to about 20 wt %, about 5 wt % to about 15 wt %, or about 8 wt % to about 12 wt %, each based on a total weight of the vesicle composition including the lipid phase and the water phase. However, embodiments are not limited thereto. When the amount of the polyol of the lipid phase is less than 5 wt %, there may be problems in terms of solubility of the lipid phase. When the amount of the polyol of the lipid phase is 30 wt % or more, problems may occur in that the vesicle may have an unpleasant sticky feeling when applied to skin.

An amount of the polyol of the water phase may be, for example, about 1 wt % to about 20 wt %, about 1 wt % to about 15 wt %, about 1 wt % to about 10 wt %, or about 3 wt % to about 10 wt %, each based on a total weight of the vesicle composition including the lipid phase and the water phase. However, embodiments are not limited thereto. When the amount of the polyol of the water phase is less than 1 wt %, a microorganism inhibition effect of the polyol may be negligible. When the amount of the polyol of the water phase exceeds 20 wt %, the vesicle may have an unpleasant sticky feeling when applied to skin.

In one or more embodiments, the amount of the ceramide or a derivative thereof may be about 0.1 wt % to about 5 wt %, the amount of the nonionic surfactant may be about 0.1 wt % to about 5 wt %, the amount of the phospholipid may be about 0.1 wt % to about 5 wt %, the amount of the polyol in the lipid phase may be about 5 wt % to about 20 wt %, the amount of the polyol in the water phase may be about 1 wt % to about 20 wt %, and an amount of the water may be equal to a remaining weight percentage, each based on a total weight of the vesicle composition including the lipid phase and the water phase. However, embodiments are not limited thereto.

In the preparing of the lipid phase, the heating may be performed at a temperature of about 50° C. to about 95° C., about 60° C. to about 95° C., about 70° C. to about 95° C., or about 80° C. to about 90° C. When the heating temperature is not within these temperature ranges, the ceramide may not dissolve or may be denatured by high temperature.

The preparing of the water phase may be performed at room temperature. However, embodiments are not limited thereto.

The lipid phase or the water phase may further include a bioactive ingredient. The term "bioactive ingredient" may refer to a material which enhances or inhibits the function of a body. The bioactive ingredient is not limited to specific types, and may include a functional material which helps skin health.

The lipid phase or the water phase may further include any ingredients commonly used in cosmetics, for example, antiseptics.

In the preparing of the vesicle by mixing and stirring the lipid phase and the water phase, the mixing may include adding the lipid phase to the water phase.

In one or more embodiments, the vesicle preparation method may further include, after the preparing of the vesicle, purifying, filtering, or separating the vesicle. The purifying, filtering, or separating may be performed using a known, commonly used method.

According to another aspect of the disclosure, there is provided a vesicle for skin absorption enhancement, the vesicle being prepared by using the method according to any of the above-described embodiments.

The vesicle according to one or more embodiments may be safe without skin irritation and have an improved skin absorption effect due to the use of the ceramide as a skin absorption enhancer, and may have improved formulation stability due to the inclusion of the nonionic surfactant and the phospholipid, such that the formulation may remain intact even at 180 days after preparation.

In one or more embodiments, the vesicle may have an average particle size of about 30 nm to about 300 nm, about 30 nm to about 250 nm, about 30 nm to about 230 nm, about 50 nm to about 300 nm, about 50 nm to about 250 nm, about 50 nm to about 230 nm, about 100 nm to about 300 nm, about 100 nm to about 250 nm, about 100 nm to about 230 nm, or about 100 nm to about 200 nm.

According to another aspect of the disclosure, there is provided a cosmetic composition including the vesicle for skin absorption enhancement according to any of the above-described embodiments.

The cosmetic composition may be prepared in any formulation commonly used in the art, for example, in the formulation of one selected from the group consisting of solutions, suspensions, emulsions, pastes, gels, creams, lotions, powders, soaps, oils, powdered foundations, emulsion foundations, waxes, and sprays. However, embodiments are not limited thereto.

The cosmetic composition may further include any additional ingredient commonly used in cosmetics, for example, one selected from thickening agents, dispersing agents, fragrance agents, filling agents, preservatives, antiseptics, neutralizing agents, sweetening agents, vitamins, free-radical scavengers, sequestering agents, functional ingredients, and mixtures thereof.

Any additional ingredients and/or amounts thereof may be chosen by one of ordinary skill in the art such that advantageous properties of the cosmetic composition according to one or more embodiments are not or substantially not to affected by the additional ingredients.

One or more embodiments of the present disclosure will now be described in detail with reference to the following examples. However, these examples are only for illustrative purposes and are not intended to limit the scope of the one or more embodiments of the present disclosure.

Example 1 and Comparative Examples 1 to 3:
Preparation of Vesicle Including Skin Absorption Enhancer Vesicles of Example 1 and Comparative Examples 1 to 3 were prepared using different skin absorption enhancers. In particular, the vesicles were prepared by slowly adding phase B, which was dissolved by heating at about 80° C. to 90° C., into phase A at ambient temperature. The vesicle of Example 1 included a ceramide as a skin absorption enhancer, while the vesicle of Comparative Example 1 did not include a skin absorption enhancer. The vesicles of Comparative Examples 2 and 3 included menthol and ethanol, respectively, as skin absorption enhancers.

The ingredients and amounts thereof in the compositions of the vesicles prepared in Example 1 and Comparative Examples 1 to 3 are provided in Table 1. Unless stated otherwise, the amounts of the ingredients are in units of wt %.

TABLE 1

| | Ingredients | Comparative Example 1 | Example 1 | Comparative Example 2 | Comparative Example 3 |
|---|---|---|---|---|---|
| A | Water | To 100 | To 100 | To 100 | To 100 |
| | Menthol | — | — | 0.3 | — |
| | Ethanol | — | — | — | 10 |
| B | Glycerin | 20 | 20 | 20 | 20 |
| | Hydrogenated lecithin | 0.3 | 0.3 | 0.3 | 0.3 |
| | Ceramide | — | 0.3 | — | — |

Test Example 1: Skin Safety Test

A skin safety test was performed on the vesicles of Example 1 and Comparative Examples 1 to 3.

In particular, 20 adults (men and women) without skin disease were made to evaluate degrees of irritation with the vesicles of Example 1 and Comparative Examples 1 to 3. After 20 μL of each sample was applied onto a forearm of each subject, the test site was closed by an occlusive tape and the patch remained for about 24 hours. Skin reactions after 30 minutes and 24 hours from removal of the patch were evaluated using the terminology presented in the guidelines of the Cosmetic, Toiletry and Fragrance Association (CTFA). Primary irritation index (PII) scores of the subjects for each vesicle, which were scored by the subjects according to evaluation criteria, were averaged and then evaluated as follows: an average score of less than 1 is regarded as a low irritation, an average score less than 2 is regarded as light irritation, an average score less than 3.5 is regarded as moderate irritation, and average score of 3.5 or greater is regarded as severe irritation.

TABLE 2

| Test item | Comparative Example 1 | Example 1 | Comparative Example 2 | Comparative Example 3 |
|---|---|---|---|---|
| Primary irritation index (PII) | 0.075 | 0.025 | 1.7 | 1.25 |

Referring to Table 2, it was found that the vesicle of Comparative Example 1 not including a skin absorption enhancer and the vesicle of Example 1 including a ceramide caused low irradiation and be commercially applicable. On the other hand, the vesicle of comparative Example 2 including menthol and the vesicle of Comparative Example 3 including ethanol were found to have a PII of 1.7 and 1.25, respectively, which correspond to a light irritation. Accordingly, the ceramide was found to be the most appropriate one of the tested skin absorption enhancers in terms of skin safety.

Examples 2 to 6: Preparation of Ceramide-Containing Vesicles

To stabilize the ceramide in the vesicles, the vesicles of Examples 2 to 6 were prepared with varying amounts of polyoxyethylene cholesteryl ether (PCE) and hydrogenated lecithin as represented in Table 3. In particular, the ceramide-containing vesicles were prepared by slowly adding phase A, which was dissolved by heating at about 80° C. to 90° C., into phase B at ambient temperature.

TABLE 3

| Phases | Ingredients | Example 2 | Example 3 | Example 4 | Example 5 | Example 6 |
|---|---|---|---|---|---|---|
| A | PCE | 1 | 0.7 | 0.5 | 0.3 | — |
| | Hydrogenated lecithin | — | 0.3 | 0.5 | 0.7 | 1 |
| | Ceramide | 0.3 | 0.3 | 0.3 | 0.3 | 0.3 |
| | Dipropylene glycol (DPG) | 10 | 10 | 10 | 10 | 10 |
| B | Water | To 100 | To 100 | To 100 | To 100 | To 100 |
| | 1,3-butylene glycol (1,3-BG) | 5 | 5 | 5 | 5 | 5 |
| | Antiseptic | q.s. | q.s. | q.s. | q.s. | q.s. |

Test Example 2: Evaluation of Stability of Ceramide-Containing Vesicle

A test of stability with time was performed on the ceramide-containing vesicles of Examples 2 to 6.

In particular, appearances and particle size distributions of the ceramide-containing vesicles of Examples 2 to 6 were observed immediately after the preparation by using a digital camera and a dynamic light scattering (DLS) instrument.

Figure 1:
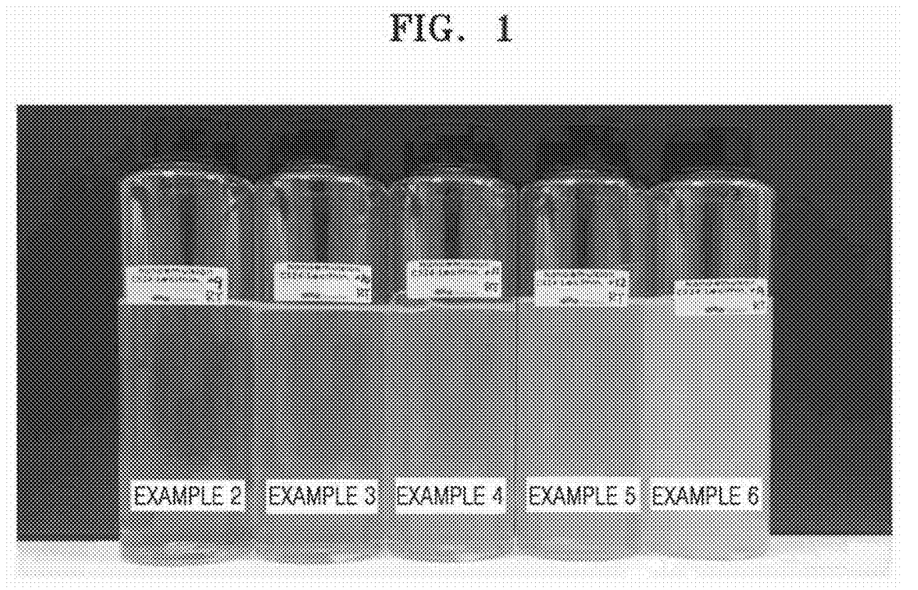
FIG. 1 is an image showing the appearance of formulations of Examples 2 to 6 immediately after preparation.

FIG. 1 is an image showing appearances of the ceramide-containing vesicles of Examples 2 to 6 immediately after preparation.

Referring to FIG. 1, the larger amount of the hydrogenated lecithin in the ceramide-containing vesicle became, the more turbidity in appearance was shown immediately after the preparation of each of the vesicles.

Table 4 represents average particle sizes (nm) of the ceramide-containing vesicles of Examples 2 to 6 measured using the DLS instrument.

TABLE 4

| | Example 2 | Example 3 | Example 4 | Example 5 | Example 6 |
|---|---|---|---|---|---|
| Average particle size (nm) | 14.7 | 147.4 | 170.3 | 190.0 | 416.2 |

Figure 2:
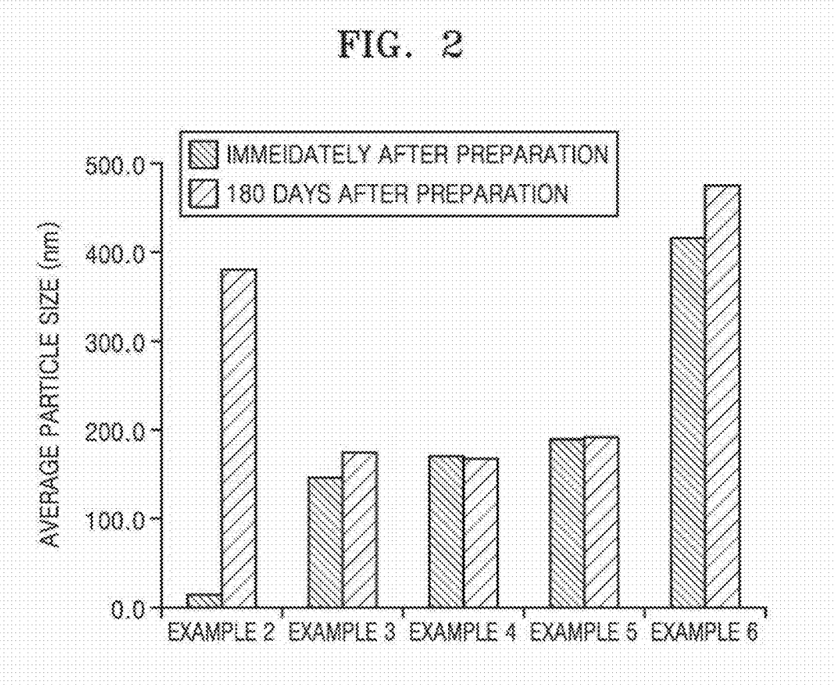
FIG. 2 illustrates results of measurement of average particle size distributions in vesicles of Examples 2 to 6, by using a dynamic light scattering (DLS) instrument, immediately after preparation of each vesicles and after storage of each preparation for 180 days under room-temperature conditions.

Referring to Table 4, the larger the amount of the hydrogenated lecithin in the ceramide-containing vesicle became, the larger average particle size was shown immediately after the preparation. These results are consistent with the results provided in FIG. 1. FIG. 2 illustrates results of measurement of average particle size distributions in the vesicles of Examples 2 to 6, by using the DLS instrument, immediately after preparation and after storage for 180 days from preparation, under room-temperature conditions.

Referring to FIG. 2, the vesicles of Examples 3 to 5 were found to be stable with nearly no change in average particle size distribution even after storage for 180 days, from the preparation, under room-temperature conditions, and in particular, the vesicles of Examples 4 and 5 were highly stable.

Test Example 3: Identification of Intermolecular Attraction Between Ceramide and Surfactant The stability with time of the ceramide-containing vesicles found in Test Example 2 was presumed to be caused by the intermolecular attraction between the ceramide and the surfactant ingredients in each vesicle. That is, the stabilization of the vesicles was attributed to the intermolecular attraction between the ceramide, PCE, and hydrogenated lecithin present at the interface of particles. To identify the presence of such intermolecular attraction, a physical mixture and a chemical mixture were prepared and the intermolecular attraction in each of the physical mixture and the chemical mixture was measured using differential scanning calorimetry (DSC) under the conditions in which the temperature was increased from 10° C. to 120° C. at a temperature increase rate of 2° C./min from.

The physical mixture and the chemical mixture for identification of the intermolecular attraction were prepared as follows. The physical mixture was prepared by simply mixing PCE, hydrogenated lecithin, and a ceramide in a single container. The chemical mixture was prepared by completely dissolving PCE, hydrogenated lecithin, and ceramide in a solvent (a 3:1 mixture of chloroform and methanol) and stirring the solution for about 1 hour such that the ingredients were chemically thoroughly mixed, evaporating the solvent with an evaporator, and completely removing the remaining solvent by using a vacuum line.

Figure 3:
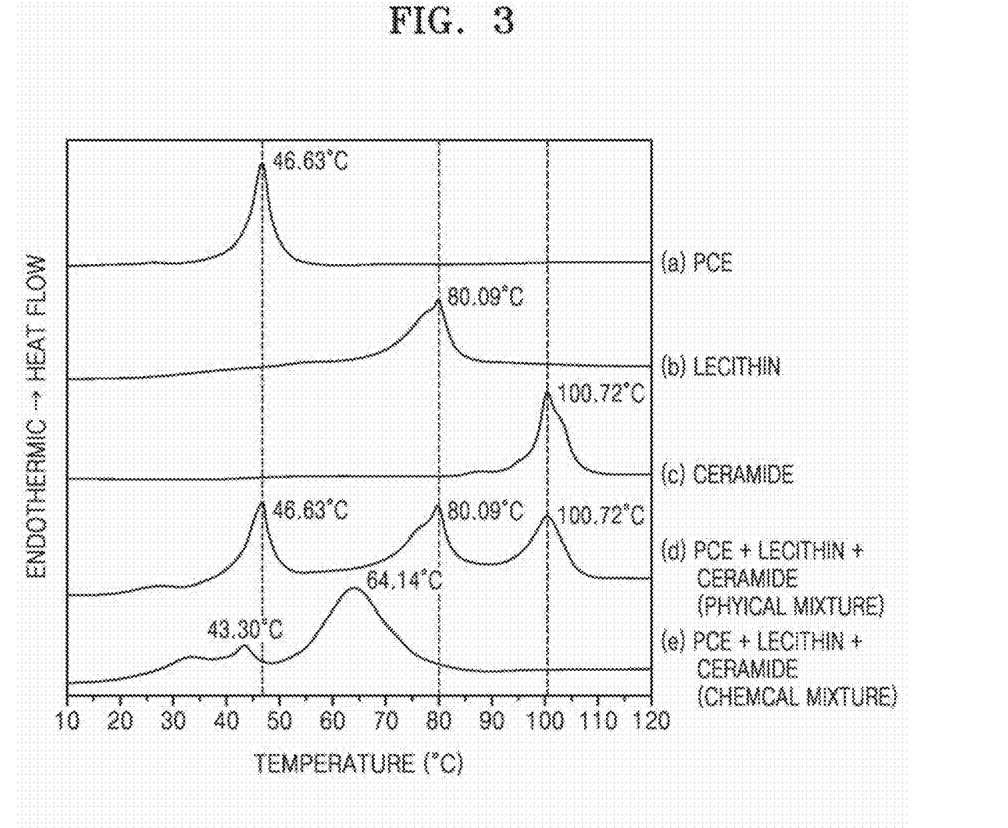
FIG. 3 illustrates results of differential scanning calorimetry (DSC) analysis of (a) polyoxyethylene cholesteryl ether (PCE), (b) hydrogenated lecithin, (c) ceramide, (d) a physical mixture of PCE, hydrogenated lecithin, and ceramide, and (e) a chemical mixture of PCE, hydrogenated lecithin, and ceramide.

FIG. 3 illustrates results of the DSC analysis of (a) PCE, (b) hydrogenated lecithin, (c) ceramide, (d) the physical mixture of PCE, hydrogenated lecithin, and ceramide, and (e) the chemical mixture of PCE, hydrogenated lecithin, and ceramide.

Referring to FIG. 3, (a) PCE, (b) hydrogenated lecithin, and (c) ceramide were found to have a melting point of about 46.63° C., about 80.09° C., and about 100.72° C., respectively. In the physical mixture (d) of PCE, hydrogenated lecithin, and ceramide, three peaks appeared, which correspond to the melting points of PCE, hydrogenated lecithin, and ceramide. However, in the chemical mixture (e) of PCE, hydrogenated lecithin, and ceramide, the peak corresponding to the melting point of ceramide disappeared, and the peak corresponding to hydrogenated lecithin was shifted to a lower temperature. This supports the presence of intermolecular attraction between PCE, hydrogenated lecithin, and ceramide at the interfaces of particles. Accordingly, it was found that, due to such intermolecular interaction, the stabilities with time of the vesicles of Examples 3 to 5 were improved as compared with those of the vesicles of Example 2 or Example 6.

Test Example 4: Identification of Ceramide Stability in Ceramide-Containing Vesicles When the stability of the ceramide in a ceramide-containing vesicles is low, gelation or crystallization of the ceramide may occur. Whether crystallization of the ceramide has occurred or not in the vesicles may be identified by X-ray analysis. Accordingly, whether crystallization of the ceramide had occurred in ceramide-containing vesicles was identified using wide-angle X-ray scattering (WAXS).

Figure 4:
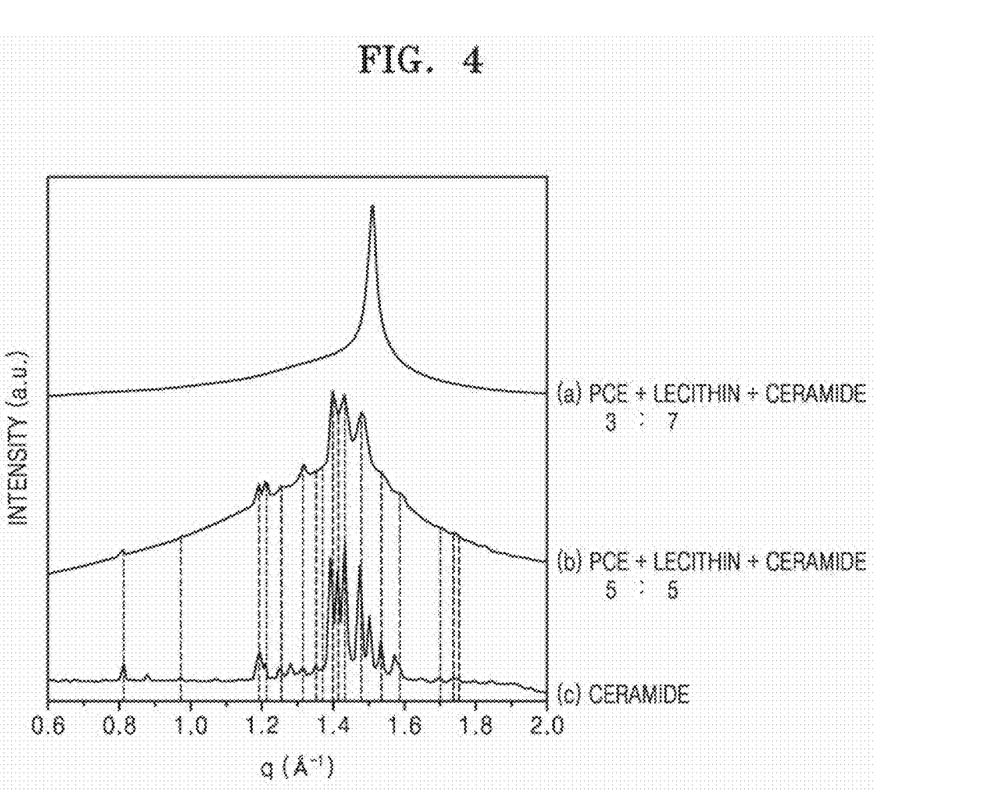
FIG. 4 illustrates results of wide-angle X-ray scattering (WAXS) analysis of (a) a chemical mixture of PCE, hydrogenated lecithin, and a ceramide with a 3:7 mixed ratio of PCE to hydrogenated lecithin as in Example 5, (b) a chemical mixture of PCE, hydrogenated lecithin, and a ceramide with a 5:5 mixed ratio of PCE to hydrogenated lecithin as in Example 4; and (c) ceramide.

FIG. 4 illustrates results of WAXS analysis of (a) a chemical mixture of PCE, hydrogenated lecithin, and ceramide with a 3:7 mixed ratio of PCE to hydrogenated lecithin as in Example 5, (b) a chemical mixture of PCE, hydrogenated lecithin, and ceramide with a 5:5 mixed ratio of PCE to hydrogenated lecithin as in Example 4; and (c) ceramide.

Referring to FIG. 4, in the chemical mixture (a) in which PCE, hydrogenated lecithin, and ceramide were chemically mixed in the same ratio as in Example 5, crystallization of the ceramide was inhibited. In contrast, in the chemical mixture (b) in which PCE, hydrogenated lecithin, and ceramide were chemically mixed in the same ratio as in Example 4, considerably crystallization of the ceramide occurred.

Although the vesicles of Examples 4 and 5 were found to be not significantly different in terms of stability, as the results of Test Example 2 in which the appearances of the vesicles were visually observed and the particle size distributions were identified by DSL, it was found that, through the WAXS analysis in Test Example 4, there was a significant difference in ceramide stability between the vesicles of Examples 4 and 5.

Example 7 and Comparative Example 4: Preparation of Ceramide-Containing Vesicle for Verification of Skin Absorption Enhancement Effect To verify a skin absorption enhancement effect of the vesicle of Example 5, which was found to have improved ceramide stability in Test Example 4, vesicles were prepared according to the compositions represented in Table 5. Retinol was used as a model drug. In particular, the vesicles were prepared by slowly adding phase A, which was dissolved by heating at about 80° C. to 90° C., into phase B at ambient temperature. The only difference between the vesicles of Comparative Example 4 and Example 7 was in ceramide content. That is, the compositions of the vesicles of Comparative Example 4 and Example 7 were used to quantify the effect that ceramide has as a skin absorption enhancer.

TABLE 5

| | Ingredients | Comparative Example 4 | Example 7 |
|---|---|---|---|
| A | PCE | 0.3 | 0.3 |
| | Hydrogenated lecithin | 0.7 | 0.7 |
| | Dipropylene glycol (DPG) | 10 | 10 |
| | Retinol | 0.15 | 0.15 |
| | Ceramide | — | 0.3 |
| B | Water | To 100 | To 100 |
| | 1,3-butylene glycol (1,3-BG) | 5 | 5 |
| | Antiseptic | q.s. | q.s. |

Test Example 5: Identification of Skin Absorption Effect Under In Vitro Conditions To evaluate skin absorption effects of the vesicles of Example 7 and Comparative Example 4 under in vitro conditions, experiments using Franz cells were conducted.

In particular, after a synthetic (Strat-M) membrane (available from Merck) was added to each open-type glass vial, appropriate amounts of the vesicles of Comparative Example 4 and Example 7 were applied to the synthetic membranes, respectively, and then left to allow sufficient penetration of the vesicles. Each acceptor portion was filled with 13 mL of a 50:50 mixture of PBS and EtOH (v/v) and then subjected to a penetration test at about 32° C. for about 24 hours. After 24 hours, the remaining vesicles on the synthetic membrane was removed by contacting an upper portion of the synthetic membrane with tape, retinol was extracted with methanol from the vesicles, and then subjected to high-performance liquid crystal (HPLC) analysis. The retinol remaining in the synthetic membrane was also extracted with methanol, followed by retinol concentration analysis using HPLC. Finally, a retinol concentration in the acceptor portion which had permeated into the synthetic membrane was also analyzed using HPLC. The tape, the synthetic membrane, and the acceptor portion represent skin absorption depths which increase in the stated order, i.e., the tape corresponds to the most shallow depth, while the acceptor portion corresponds to the deepest. HPLC analysis conditions are illustrated in Table 6.

TABLE 6

| Column | $C_{18}$ (250 × 4.6 mm, 5 μm, 300 A, Jupiter) |
|---|---|
| Detector | Reversed phase high-pressure liquid chromatography (UltiMate 3000, Dionex) |
| Flow rate | 1.0 mL/min |
| Absorbance | 325 nm |
| Mobile phase | 90% methanol, isocratic elution |

Figure 5:
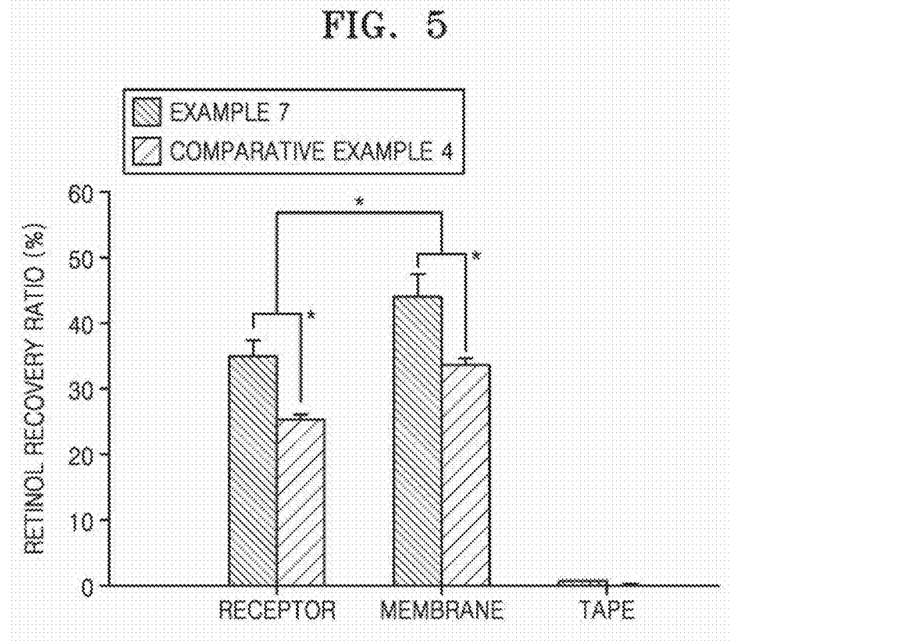
FIG. 5 illustrates in vitro evaluation results of skin absorption effects of the vesicles of Example 7 and Comparative Example 4.

FIG. 5 illustrates in vitro evaluation results of skin absorption effect of the vesicles of Example 7 and Comparative Example 4.

Referring to FIG. 5, the vesicles of Example 7 including ceramide was found to exhibit improved skin absorption under in vitro conditions, as compared with the vesicles of Comparative Example 4. In particular, a higher retinol recovery ratio of the vesicles of Example 7 at the acceptor portion, as compared with that of the vesicles of Comparative Example 4, means that skin absorption of the vesicles of Example 7 proceeded much further as compared with the vesicles of Comparative Example 4.

Test Example 6: Identification of Skin Absorption Effect Under In Vivo Conditions To evaluate skin absorption effects of the vesicles of Example 7 and Comparative Example 4 under in vivo conditions, a clinical test of skin absorption was performed using confocal Raman spectroscopy.

In particular, test subjects were 10 healthy women aged 35 to 40 years, with an average age of 37.9. The test was performed before application of each vesicles, immediately after the application, and after 30 minutes, 1 hour, and 2 hours from the application. Each vesicles was applied onto a test site of each subject in an amount of about 50 μL/cm² and then sufficiently absorbed for about 20 minutes, and the vesicles remaining unabsorbed was removed with a tissue. Then, the test site was analyzed using a confocal Raman spectrometer, from the outermost layer of the skin to a depth of about 24 μm at intervals of about 2 μm, repeatedly each five times. Retinol used as a model drug typically exhibits a featured Raman peak at about 1596 $cm^{-1}$. The Raman peak intensity on the Y-axis with respect to time in Raman spectra is an index of the level of skin absorption. The used confocal Raman spectrometer was a skin composition analyzer (Model 3510 SCA, available from River Diagnostics, Netherlands).

Figure 6:
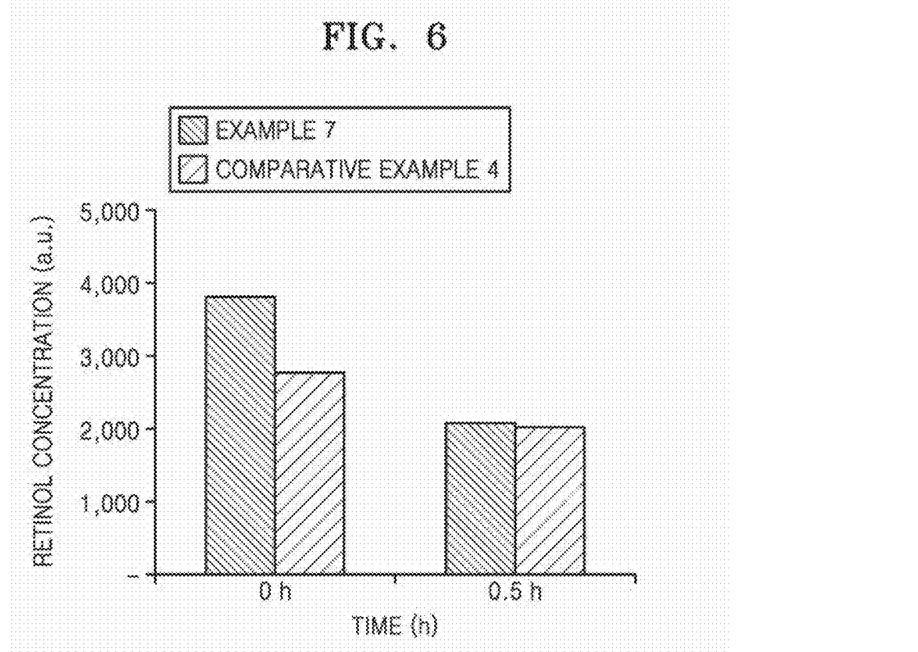
FIG. 6 illustrates in vivo evaluation results of skin absorption effects of the vesicles of Example 7 and Comparative Example 4.

FIG. 6 illustrates in vivo evaluation results of skin absorption effect of the vesicles of Example 7 and Comparative Example 4.

Referring to FIG. 6, the vesicle formulation of Example 7 was found to have improved skin absorption under the in vivo conditions, as compared with that of Comparative Example 4, indicating a skin absorption enhancement effect of the ceramide.

As described above, according to the one or more embodiments, the vesicle preparation method may provide a skin absorption enhancement effect and may prepare vesicles with improved formulation stability. Vesicles prepared using the method may be safe without skin irritation and have an improved skin absorption effect due to use of ceramide as a skin absorption enhancer, and may have improved formulation stability due to use of a nonionic surfactant and phospholipid. The vesicles may be used in cosmetic compositions for enhancing skin absorption of bioactive ingredients such as functional ingredients.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of preparing vesicles, the method comprising:
   heating and dissolving ceramide or a derivative thereof, polyoxyethylene cholesteryl ether (PCE), a phospholipid, and a polyol to thereby prepare a lipid phase;
   preparing a water phase including a polyol and water; and
   mixing and then stirring the lipid phase and the water phase to thereby prepare the vesicles, wherein the vesicles do not contain cholesterol.

2. The method of claim 1, wherein the phospholipid is lecithin or hydrogenated lecithin.

3. The method of claim 1, wherein the polyol of the lipid phase and the polyol of the water phase are each independently at least one selected from the group consisting of propylene glycol, dipropylene glycol, 1,3-butylene glycol, pentylene glycol, and 1,2-hexanediol.

4. The method of claim 1, wherein an amount of the ceramide or a derivative thereof is about 0.1 wt % to about 5 wt %, an amount of PCE is about 0.1 wt % to about 5 wt %, an amount of the phospholipid is about 0.1 wt % to about 5 wt %, an amount of the polyol in the lipid phase is about 5 wt % to about 20 wt %, an amount of the polyol in the water phase is about 1 wt % to about 20 wt %, and an amount of the water is equal to a remaining weight percentage, each based on the total weight of the vesicles comprising the lipid phase and the water phase.

5. The method of claim 1, wherein a weight ratio of PCE to the phospholipid is about 1:10 to about 10:1.

6. Vesicles for skin absorption enhancement, the vesicles being prepared by the method according to claim 1.

7. A cosmetic composition comprising the vesicles for skin absorption enhancement according to claim 6.

8. The cosmetic composition of claim 7, wherein the cosmetic composition is in the formulation of any one selected from the group consisting of solutions, suspensions, emulsions, pastes, gels, creams, lotions, powders, soaps, oils, powdered foundations, emulsion foundations, waxes, and sprays.

* * * * *